United States Patent
Hampton et al.

(10) Patent No.: US 11,141,102 B2
(45) Date of Patent: Oct. 12, 2021

(54) SYSTEM AND METHOD TO MEASURE, ANALYZE, AND MODEL PULMONARY FUNCTION AND DISEASE UTILIZING TEMPORAL, SPATIAL, AND CONTEXTUAL DATA

(71) Applicant: International Business Machines Corporation, Armonk, NY (US)

(72) Inventors: Mark C. Hampton, Melbourne (AU); Timothy M. Lynar, Kew (AU); Suraj Pandey, Melbourne (AU); John M. Wagner, Plainville, CT (US)

(73) Assignee: International Business Machines Corporation, Armonk, NY (US)

( * ) Notice: Subject to any disclaimer, the term of this patent is extended or adjusted under 35 U.S.C. 154(b) by 1062 days.

(21) Appl. No.: 15/397,258

(22) Filed: Jan. 3, 2017

(65) Prior Publication Data
US 2017/0112430 A1    Apr. 27, 2017

Related U.S. Application Data

(62) Division of application No. 14/495,348, filed on Sep. 24, 2014, now Pat. No. 10,201,307.

(51) Int. Cl.
*A61B 5/00* (2006.01)
*G10L 25/66* (2013.01)
(Continued)

(52) U.S. Cl.
CPC .......... *A61B 5/4803* (2013.01); *A61B 5/0022* (2013.01); *A61B 5/087* (2013.01);
(Continued)

(58) Field of Classification Search
CPC ................. G06F 19/00; G06F 19/3418; G06F 17/30702; A61B 5/087; A61B 5/6898;
(Continued)

(56) References Cited

U.S. PATENT DOCUMENTS 6,139,505 A     1/2000  Murphy
6,289,313 B1 *  9/2001  Heinonen ............... G10L 17/26
                                                      600/301
(Continued)

OTHER PUBLICATIONS

Notice of Allowance for U.S. Appl. No. 14/495,348 dated Oct. 2, 2018.
(Continued)

*Primary Examiner* — Christian Jang
*Assistant Examiner* — Karen E Toth
(74) *Attorney, Agent, or Firm* — Fleit Intellectual Property Law; Jose Gutman

(57) ABSTRACT

An information processing system, computer readable storage medium, and methods for analyzing the airflow related health of a person. A method includes obtaining an audio sample of a person's verbal communication, obtaining geographic information of the person, querying a remote server based on the geographic information, and obtaining additional information from the remote server, the additional information being related to the geographic information, and extracting contours of amplitude change from the at least one audio sample over a period of time, the contours of amplitude change corresponding to changes in an airflow profile of the person. The method further includes correlating the contours of amplitude change with periodic episodes typical of airflow related health problems, and determining, based at least on the additional information, whether the contours of amplitude change result from at least one local environmental factor related to the geographic information.

8 Claims, 7 Drawing Sheets

(51) Int. Cl.
| | |
|---|---|
| *A61B 5/087* | (2006.01) |
| *A61B 5/11* | (2006.01) |
| *G16H 40/67* | (2018.01) |
| *G16H 50/70* | (2018.01) |
| *H04W 4/80* | (2018.01) |
| *G06F 19/00* | (2018.01) |

(52) U.S. Cl.
CPC .......... *A61B 5/1112* (2013.01); *A61B 5/7246* (2013.01); *G06F 19/00* (2013.01); *G10L 25/66* (2013.01); *G16H 40/67* (2018.01); *A61B 5/6898* (2013.01); *A61B 2560/0247* (2013.01); *G16H 50/70* (2018.01); *H04W 4/80* (2018.02)

(58) Field of Classification Search
CPC ... A61B 5/0022; A61B 5/4803; A61B 5/7246; A61B 5/7275; A61B 5/0002; A61B 5/08; A61B 5/7282; G16H 50/20; G16H 50/30; G16H 50/70; G10L 25/66; H04W 4/02; H04W 4/38; H04W 4/80
See application file for complete search history.

(56) References Cited

U.S. PATENT DOCUMENTS

| | | |
|---|---|---|
| 2006/0285660 A1 | 12/2006 | Brown |
| 2008/0109158 A1* | 5/2008 | Huhtala ............. A63B 24/0062 701/439 |
| 2011/0092779 A1 | 4/2011 | Chang et al. |
| 2012/0116241 A1* | 5/2012 | Shieh .................... A61B 5/082 600/532 |
| 2014/0032596 A1 | 1/2014 | Fish et al. |
| 2015/0379400 A1 | 12/2015 | Tatourian et al. |

OTHER PUBLICATIONS

Abaza, A., et al., "Classification of voluntary cough sound and airflow patterns for detecting abnormal pulmonary function," Published Nov. 20, 2009, pp. 1-6, Copyright 2009 Abaza et al; licensee BioMed Central Ltd. doi:10.1186/1745-9974-5-8.

* cited by examiner

| USER PULMONARY HEALTH TRACKING DATABASE | | | | | |
|---|---|---|---|---|---|
| USER ID | PROFILE | HISTORY | SPEECH CHARACTERISTICS MODEL(S) | DEVICE(S) NETWORK ID INFORMATION | CONTEXTUAL INFORMATION | OTHER DATA |
| 1 | | | | | | |
| 2 | | | | | | |
| 3 | | | | | | |
| 4 | | | | | | |
| 5 | | | | | | |
| 6 | | | | | | |
| 7 | | | | | | |
| 8 | | | | | | |
| 9 | | | | | | |
| 10 | | | | | | |

FIG. 3

USER PULMONARY HEALTH HISTORY DATABASE

| SNAPSHOT ID 502 | TIME FRAME 504 | SPEECH-RELATED CHARACTERISTIC 506 | LOCATION 508 | WEATHER CONDITIONS 510 | PARTICULATE COUNTS & CONDITIONS 512 | OTHER CONTEXTUAL INFORMATION 514 | AIRFLOW RELATED EPISODES 516 | SPEAKING ACTIVITIES 518 | OTHER HEALTH DATA 520 |
|---|---|---|---|---|---|---|---|---|---|
| 1 | | | | | | | | | |
| 2 | | | | | | | | | |
| 3 | | | | | | | | | |
| 4 | | | | | | | | | |
| 5 | | | | | | | | | |
| 6 | | | | | | | | | |
| 7 | | | | | | | | | |
| 8 | | | | | | | | | |
| 9 | | | | | | | | | |
| 10 | | | | | | | | | |
| 11 | | | | | | | | | |
| 12 | | | | | | | | | |

FIG. 5

SYSTEM AND METHOD TO MEASURE, ANALYZE, AND MODEL PULMONARY FUNCTION AND DISEASE UTILIZING TEMPORAL, SPATIAL, AND CONTEXTUAL DATA

BACKGROUND

The present disclosure generally relates to measurement and analysis of temporal, spatial, and contextual effects on lung function of individuals, and more particularly relates to a method and system for measuring changes in characteristics of an individual's speech and vocal tract related air flow and from those measurements, along with other related temporal, spatial, and contextual information, determining the presence of triggers for airflow related disease, and informing individuals regarding such triggers.

Pulmonary health and capacity can be seriously impacted by various types of pulmonary disease and by external disease triggers such as, but not limited to, pollen count, smog, and various types of air pollution.

The most common symptoms of asthma include shortness of breath, wheezing, chest tightness and a dry, irritating, continual cough, all caused at least in part by narrowing of the airway. Chronic obstructive pulmonary disease, involves a gradual progression from inflation to the small airways that limits airflow to the destruction of alveolar walls and capillaries which leads to loss of elasticity. Symptoms of emphysema therefore include a distinctive cough and shortness of breath.

Triggers for acute disease can have drastic immediate effects on individuals. Likewise triggers that affect chronic disease on a day to day basis can have a substantial effect on an individual. Knowledge of what and where these triggers are and how to avoid or mitigate them can be very powerful information for afflicted individuals.

BRIEF SUMMARY

According to one embodiment of the present disclosure, a method for analyzing the airflow related health of a person, the method comprising: obtaining at least one audio sample of a person's verbal communication; obtaining geographic information of the person, the geographic information being associated with the at least one audio sample of the person's verbal communication; querying at least one additional source of information based on the geographic information, and as a result of the querying obtaining additional information from the at least one additional source of information, the additional information being related to the geographic information; extracting contours of amplitude change from the at least one audio sample over a period of time, the contours of amplitude change corresponding to changes in an airflow profile of the person; correlating the contours of amplitude change with periodic episodes typical of airflow related health problems; and determining, based at least on the additional information, whether the contours of amplitude change result from at least one local environmental factor related to the geographic information.

According to another embodiment of the present disclosure, an information processing system is capable of analyzing the airflow related health of a person. The information processing system comprises: a microphone circuit for receiving audio signals from an ambient environment in vicinity of the information processing system, and converting the audio signals to electronic audio signals; analog-to-digital conversion circuits, coupled with the microphone circuit, for converting the electronic audio signals to digitized audio signals; memory; non-volatile memory for storing data and computer instructions; a pulmonary health monitor, communicatively coupled with the non-volatile memory; a user pulmonary health current profile, communicatively coupled with the non-volatile memory; a user's speech characteristics model, communicatively coupled with the non-volatile memory; a contextual information database, communicatively coupled with the non-volatile memory; a processor, communicatively coupled with the analog-to-digital conversion circuits, the memory, the non-volatile memory, and the pulmonary health monitor, and wherein the processor, responsive to executing computer instructions, performs operations comprising: obtaining at least one audio sample of a person's verbal communication, captured from the ambient environment in vicinity of the information processing system; obtaining geographic information of the person, the geographic information being associated with the at least one audio sample of the person's verbal communication; querying at least the contextual information database based on the geographic information, and as a result of the querying obtaining additional information from the contextual information database, the additional information being related to the geographic information; extracting contours of amplitude change from the at least one audio sample over a period of time, the contours of amplitude change corresponding to changes in an airflow profile of the person, the airflow profile of the person being stored in at least one of the user's speech characteristics model and the user pulmonary health current profile; correlating the contours of amplitude change with periodic episodes typical of airflow related health problems; and determining, based at least on the additional information, whether the contours of amplitude change result from at least one local environmental factor related to the geographic information.

According yet to another embodiment of the present disclosure, a computer readable storage medium comprises computer instructions which, responsive to being executed by a processor, cause the processor to perform operations comprising: obtaining at least one audio sample of a person's verbal communication; obtaining geographic information of the person, the geographic information being associated with the at least one audio sample of the person's verbal communication; querying at least one additional source of information based on the geographic information, and as a result of the querying obtaining additional information from the at least one additional source of information, the additional information being related to the geographic information; from the at least one audio sample, extracting contours of amplitude change over a period of time that can be mapped to changes in an airflow profile of the person; correlating the contours of amplitude change with periodic episodes typical of airflow related health problems; and determining, based at least on the additional information, whether the contours of amplitude change result from at least one local environmental factor related to the geographic information.

BRIEF DESCRIPTION OF THE SEVERAL VIEWS OF THE DRAWINGS

The accompanying figures, in which like reference numerals refer to identical or functionally similar elements throughout the separate views, and which together with the detailed description below are incorporated in and form part of the specification, serve to further illustrate various embodiments and to explain various principles and advantages all in accordance with the present disclosure, in which:

FIG. 3 is a block diagram illustrating an example of a user pulmonary health tracking database as shown in FIG. 1, according to various examples of the present disclosure;

FIG. 5 is a block diagram illustrating an example of a user pulmonary health history database as shown in FIG. 2, according to various examples of the present disclosure;

DETAILED DESCRIPTION

Figure 1:
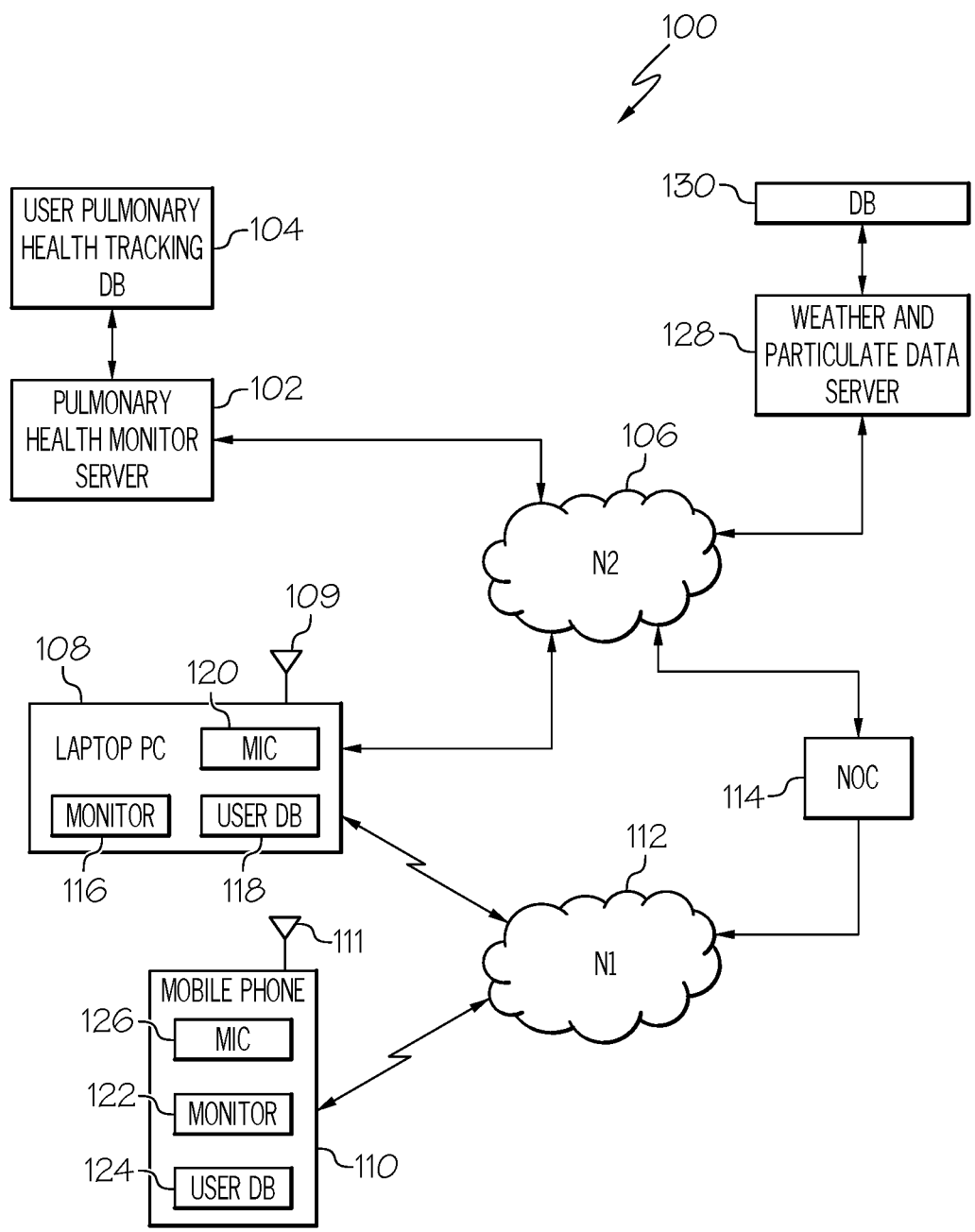
FIG. 1 is a block diagram illustrating an example of a communication system in which an information processing system can operate according to methods of the present disclosure.

According to various embodiments of the present disclosure, disclosed is a system and method to measure and analyze temporal, spatial, and contextual affects on lung function of a person. Proposed is an information processing system to measure the temporal changes in speech characteristics of a user, inferring lung function from those measurements, and performing temporal and spatial analysis on this data. Specifically, according to one embodiment, a smart mobile device equipped with microphones and location services can be used to detect and analyze the volume, tempo, intonation, emphasis, sentence and word length, and other speech characteristics produced by the mobile device user. The smart mobile device, according to certain embodiments, can correlate these characteristics to detect changes in characteristics that infer acute symptoms of pulmonary diseases, as well as that can indicate the progression of chronic pulmonary disease. Changes in characteristics can be mapped, temporally and spatially, with reference to context information to detect triggers of the changes. The smart mobile device can detect changes in airflow through detection of changes in the characteristics of a mobile device user's speech. The smart mobile device uses the detected information to inform a person, such as the user of the smart mobile device, concerning pulmonary disease of the person using the smart mobile device, and how that disease is affected by weather, geography, and other contextual data such as a level of airborne particulate matter concentration (e.g., pollen, smog, and pollutants) in a geographic region.

According to various embodiments, the smart mobile device generates and/or updates a model of the characteristics of the user's speech. The smart mobile device uses the model to determine how these characteristics, and changes thereto, relate to pulmonary health and airflow capacity of a person using the smart mobile device, and how these characteristics relate to the other contextual data sources, such as geographic data, weather, presence of particulates in the atmosphere, and other likely pulmonary disease triggers.

The most common symptoms of asthma include shortness of breath, wheezing, chest tightness and a dry, irritating, continual cough, all caused at least in part by narrowing of the airway. Chronic obstructive pulmonary disease, involves a gradual progression from inflation to the small airways that limits airflow to the destruction of alveolar walls and capillaries which leads to loss of elasticity. Symptoms of emphysema therefore include a distinctive cough and shortness of breath.

Triggers for acute disease can have drastic effects on individuals, knowledge of what and where these triggers are and how to avoid or mitigate them can be very powerful.

Likewise, factors that affect chronic disease on a day to day basis can have a substantial effect on an individual's pulmonary health and well being. Proposed is a system that helps empower users as decision makers in the management of their pulmonary disease and health, using a wide array of information sources including physiological, geographical, historical, and contextual data that can be queried from sources of information.

Various embodiments of the present disclosure monitor the trend of a users' speech such as word use and sentence structure to derive a peak airflow value of a user and model this value over time in conjunction with environmental data including the weather, particulate data, location data etc, to build a model of a user including their pulmonary function. This model is used to derive potential contextual trigger events to acute declines in the user's pulmonary function and to provide feedback to the user and/or their health care provider.

Referring to FIG. 1, an example communication system 100 is shown, according to various embodiments of the present disclosure. A pulmonary health monitor server 102 is communicatively coupled with a user pulmonary health tracking database 104. The pulmonary health monitor server 102 is communicatively coupled with a wide area network N2 106. The wide area network N2 106, in this example, can comprise one or more networks (e.g., any combination of local area network(s) and wide area networks) distributed over a wide geographic area.

A laptop PC 108, according to the present example, is communicatively coupled with the wide area network N2 106. In the example, the laptop PC 108 is communicatively coupled with the wide area network N2 106 via a wired communication interface. However, other types of communication interfaces are equally applicable for facilitating communication between the laptop PC 108 and the wide area network N2 106. The laptop PC 108 comprises wireless communication circuits and at least one antenna 109 that facilitate the laptop PC 108 communicating with at least one wireless communication network N1 112, as shown.

In the present example, a mobile phone 110 is communicatively coupled with the wireless communication network N1 112. The mobile phone 110 includes at least one antenna 111 that facilitates wireless communication with the wireless communication network N1 112. The mobile phone 110 is able to make telephone calls and receive telephone calls over the wireless communication network N1 112. Additionally, the mobile phone 110 can wirelessly transmit and receive messages over the wireless communication network N1 112 to other information processing systems and devices.

Each of the laptop PC 108 and the mobile phone 110 respectively includes a microphone 120, 126, a user pulmonary health profile database 118, 124, and a pulmonary health monitor 116,122, as shown in the example of FIG. 1. These elements of the laptop PC 108 and the mobile phone 110 will be discussed in more detail below.

The wireless communication network N1 112 is managed through a network operating center (NOC) 114 that controls and coordinates communications with information processing systems and wireless devices that are using the wireless communication network N1 112. The NOC 114 also provides a network communication interface between the at least one wireless communication network N1 112 and the wide area network 106, as shown. For example, according to various embodiments, the laptop PC 108 and the mobile phone 110 can wirelessly transmit and receive messages over the wireless communication network N1 112, and via the NOC 114 over the wide area network N2 106, to-from other remotely located information processing systems and devices.

A weather and particulate data server 128, according to the present example, is communicatively coupled with a corresponding weather and particulate database 130. The weather and particulate server 128 is communicatively coupled with the wide area network N2 106 as shown. The weather and particulate server 128, operating in communication with the corresponding weather and particulate database 130, provides contextual data in response messages that are sent in response to request messages received from information processing systems and devices that may be located remotely across the wide area network N2 106, as will be discussed in more detail below.

Figure 2:
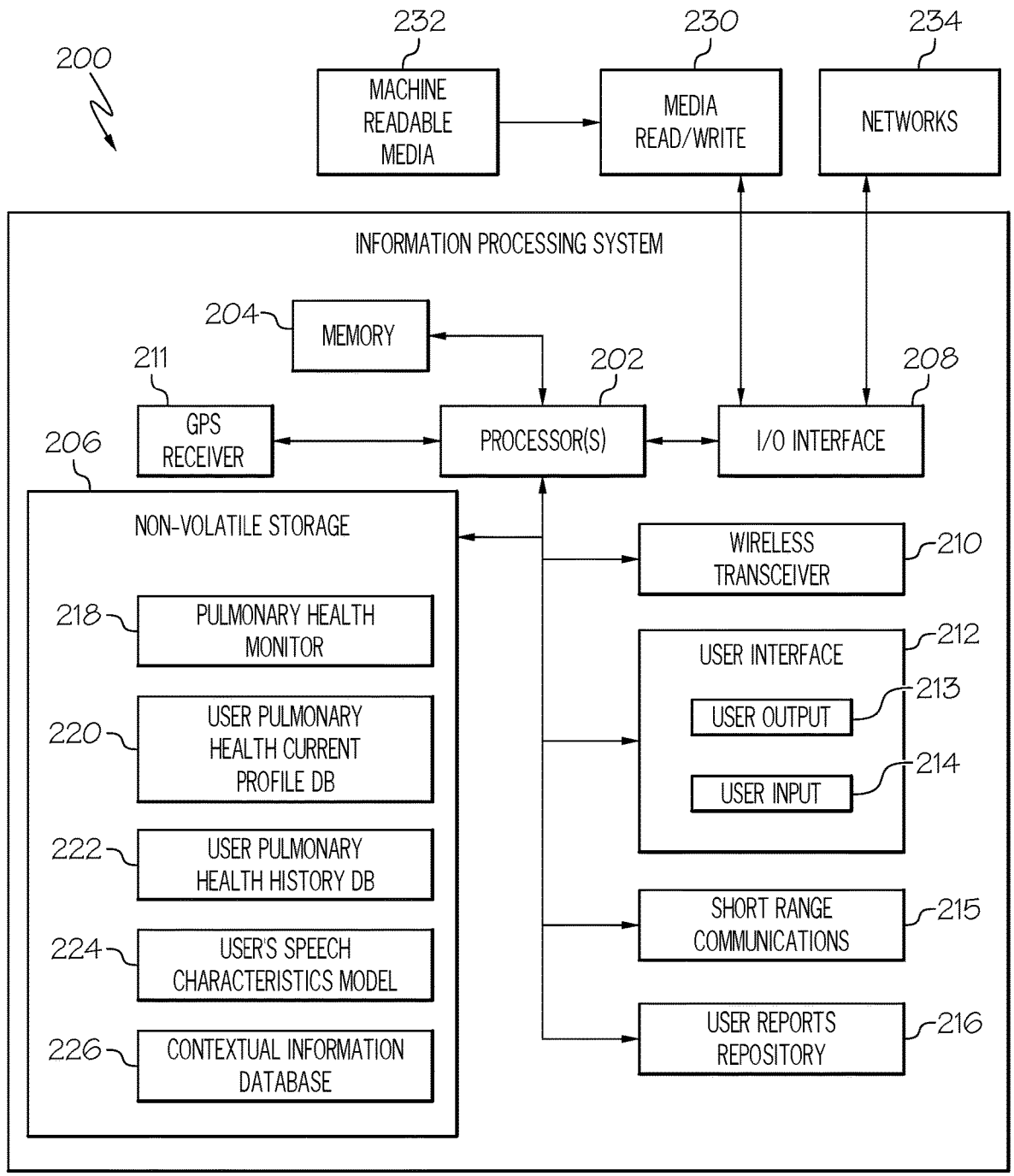
FIG. 2 is a block diagram illustrating an example of an information processing system according to various embodiments of the present disclosure.

An information processing system 200 is shown in FIG. 2 according to one example. The information processing system 200 may comprise, according to various embodiments of the present disclosure, at least one of an information processing system, a mobile phone, a personal computer, a laptop PC, a tablet PC, and other types of information processing systems and devices, as will be discussed below.

The information processing system 200 includes at least one processor 202. The at least one processor 202 is communicatively coupled with main memory 204 and with non-volatile memory 206. An input-output interface 208 is communicatively coupled with the processor 202 and provides an interface with external networks 234 as shown. The external networks 234, according to various embodiments, may include the wide area network N2 106 and the at least one wireless communication network N1 112. The input-output interface 208 can also be communicatively coupled with a media reader-writer 230. The media reader-writer 230 can be communicatively coupled with a computer-readable storage medium 232 allowing the processor 202 to read data and computer instructions from, and optionally write data and computer instructions to, the computer-readable storage medium 232.

The non-volatile storage 206 can store data, configuration parameters, and computer instructions, that are useable by the processor 202. A pulmonary health monitor 218 is stored in the non-volatile storage 206. The pulmonary health monitor 218 can interoperate with the processor 202 to provide novel functions and features of the information processing system 200, according to various embodiments of the present disclosure.

A user pulmonary health profile database 220 is stored in the non-volatile storage 206 and communicatively coupled with the processor 202. The user pulmonary health profile database 220 comprises current (i.e., short term) pulmonary health profile data associated with one or more persons that are users of the information processing system 200. For example, and not for limitation, user pulmonary health profile data may be maintained for each user for the past several minutes, hours, today, or possibly the last few days, such that it represents a current profile of the user's pulmonary health.

A user pulmonary health history database 222 is stored in the non-volatile storage 206 and communicatively coupled with the processor 202. The user pulmonary health history database 222 includes user pulmonary health data that is tracked for each person that is a user of the information processing system 200 over an extended period of time (i.e., long term). For example, and not for limitation, user pulmonary health history may be maintained and tracked for one or more users for the past several days, weeks, months, or over the life of the user's use of the information processing system 200. Each user is tracked with their own pulmonary health history database 222.

A user's speech characteristics model 224 is stored in the non-volatile storage 206 (and accordingly is communicatively coupled with the processor 202) for each person who is a user of the particular information processing system 200. The user's speech characteristics model 224 provides information related to a particular person's speech characteristics which can be used, along with temporal, spatial, and contextual information that can affect lung function and airflow disease of a person. For example, a user's speech characteristics can include the particular person's voiced and non-voiced speech audio volume, tempo, intonation, emphasis, sentence and word length, and other speech characteristics produced by the person who is a user of the particular information processing system 200.

It should be noted that a user's speech characteristics could vary between the person's use of different information processing systems 200. For example, a person that uses the mobile phone 110 and also uses the laptop PC 108 at different times to communicate their speech audio, may have stored in each of the mobile phone 110 and the laptop PC 108 two different user's speech characteristics models 224 for the same person. This variation in the two models 224 can be caused, for example, by the different audio input interface and speech processing circuitry in the mobile phone 110 as compared with the laptop PC 108. Also, the person's mouth location relative to a microphone and the person's posture during speaking can significantly vary between the person's use of the mobile phone 110 as compared with their use of the laptop PC 108. Additionally, the environment in which a user normally uses the mobile phone 110 can vary from the environment in which the user uses the laptop PC 108. For example, the laptop PC 108 may be normally used while indoors, while the mobile phone 110 may be used more on-the-go while outdoors. There are many factors that can affect the user's speech characteristics while using a particular information processing system 200. Accordingly, multiple user's speech characteristics models 224 could be dynamically maintained for the same user that uses multiple information processing systems 200, one model 224 associated with each system 200.

A contextual information database 226 is stored in the non-volatile storage 206. The contextual information database 226 maintains various types of contextual information, such as, but not limited to, geographic data, weather information, prevalence of airborne particulate matter, pollen count, and likely airflow disease triggers, and also such contextual data as the level of background noise experienced in a particular geographic location, the amount of speech-related activities (e.g., number of phone calls, meetings, etc.) the person made during certain times at a particular geographic location. The processor 202 can query the contextual information database 226 based on the geographic information of the person using the mobile phone 110, and as a result of the querying can obtaining additional information from the contextual information database. Contextual information can be analyzed in combination with the person's speech characteristics, to analyze an audio sample obtained from a person's verbal communication for determining a user's pulmonary health and airflow disease and likely (e.g., determined likely from past monitored experiences and predicted information for particular tracked geographic information) presence of triggers of airflow disease, as will be discussed in more detail below.

With continued reference to FIG. 2, the information processing system 200 includes a wireless transceiver 210 communicatively coupled with the processor 202, which facilitates the processor 202 communicating over one or more wireless communication networks such as the wireless communication network N1 112 shown in FIG. 1. The wireless transceiver 210 can support short-range or long-range wireless access technologies such as Bluetooth, Zigbee, Wi-Fi, Digital Enhanced Cordless Telecommunications (DECT), or cellular communication technologies, just to mention a few. Cellular communication technologies can include, for example, code division multiple access-1 X (CDMA-1 X), Universal Mobile Telephone System/High Speed Downlink Packet Access (UMTS/HSDPA), Global System for Mobile/General Packet Radio System (GSM/GPRS), time division multiple access/Enhanced Data GSM Environment (TDMA/EDGE), Evolution Data Optimized (EV/DO), Worldwide Interoperability for Microwave Access (WiMAX), Software Defined Radio (SDR), Long Term Evolution (LTE), as well as other next generation wireless communication technologies as they arise. The wireless transceiver 210 can also be adapted to support circuit-switched wireline access technologies (such as Public Switched Telephone Network (PSTN)), packet-switched wireline access technologies (such as Transmission Control Protocol/Internet Protocol (TCP/IP), Voice over Internet Protocol (VoIP), etc.), and combinations thereof.

The processor 202 is communicatively coupled with a user-interface 212. The user interface 212 includes a user output interface 213 and a user input interface 214.

The user input interface 214 can include a depressible, touch-sensitive or virtual keypad (or keyboard) with a navigation mechanism such as a roller ball, an optical navigation module (i.e. trackpad), a joystick, a mouse, or a navigation disk for manipulating operations of the information processing system 200. The keypad can be an integral part of a housing assembly of the information processing system 200 (e.g., part of a housing for the mobile phone 110 or the laptop PC 108) or an independent device operably coupled thereto by a tethered wireline interface (such as a Universal Serial Bus (USB) cable) or a wireless interface supporting, for example, Bluetooth. The keypad can represent a numeric keypad commonly used by phones, and/or a QWERTY keypad with alphanumeric keys. The keypad can also represent a single button or switch that can invoke function(s) of the information processing system 200 upon a activation of the single button or switch.

The user input interface 214 can further include a microphone circuit and associated audio conditioning and processing circuitry such as analog-to-digital conversion circuits, coupled with the microphone circuit. The microphone circuit receives audio signals from an ambient environment in vicinity of the microphone circuit (e.g., in vicinity of the mobile phone 110, the laptop PC 108, and the like), and converting the audio signals to electronic audio signals. The analog-to-digital conversion circuits are operable for converting the electronic audio signals to digitized audio signals. The microphone circuit and associated audio conditioning and processing circuitry can be used for receiving audible signals of a person who is a user of the information processing system 200. According to certain embodiments, the microphone circuit and associated audio conditioning and processing circuitry can also be used for voice recognition applications such as to receive voiced commands and information from a user.

The user input interface 214 can also include an environmental sensor that can include an accelerometer, a gyroscope, a GPS sensor, an inclinometer, an optical sensor, audio-spectrum sensors, ultrasonic transmitters and sensors, an infrared or other proximity sensor, or another sensor which can detect orientation or motion. The environmental sensor can also include a thermometer, a pressure gauge, or other environmental sensor.

The user output interface 213 can include a display such as a monochrome or color Liquid Crystal Display (LCD), Organic Light Emitting Diode (OLED) or other suitable display technology for conveying images to a user of the information processing system 200. In an embodiment where the display is touch-sensitive, a portion or all of the keypad can be presented by way of the display with navigation features.

The display can use touch screen technology to also serve as a user interface for detecting user input (e.g., touch of a user's finger). As a touch screen display, the information processing system 200 can be adapted to present a user interface with graphical user interface (GUI) elements that can be selected by a user with a touch of a finger. The touch screen display can be equipped with capacitive, resistive or other forms of sensing technology to detect how much surface area of a user's finger has been placed on a portion of the touch screen display. This sensing information can be used to control the manipulation of the GUI elements. The display can be an integral part of the housing assembly of the information processing system 200 or an independent device communicatively coupled thereto by a tethered wireline interface (such as a cable) or a wireless interface.

The user output interface 213 can further include an audio system that utilizes audio technology for conveying low volume audio (such as audio heard in proximity of a human ear) and high volume audio (such as speakerphone for hands free operation). The environmental sensor 113 within the UI 104 can also be a charged coupled device (CCD) camera for capturing still or moving images or for just capturing ambient light conditions.

The processor 202 is communicatively coupled with a location receiver 211 (e.g., a GPS receiver 211 is shown in the example of FIG. 2) which can utilize common location technology such as a global positioning system (GPS) receiver capable of assisted GPS for identifying a location of the information processing system 200 (e.g., the mobile phone 110, the laptop PC 108, and the like) based on signals generated by a constellation of GPS satellites, which can be used for facilitating location services such as navigation and geographic positioning.

In the example of FIG. 2, the processor 202 is communicatively coupled with short-range communications circuitry 215 which allows the processor 202 to communicate with other information processing systems and devices in the near vicinity of the information processing system 200. For example, the short-range communications circuitry 215 may include an infrared device and associated circuits and components or a Radio Frequency based communication module such as one supporting Bluetooth® communications, to provide for communication with similarly-enabled systems and devices.

A user-reports repository 216 is communicatively coupled with the processor 202. The user-reports repository 216 stores one or more user pulmonary health (e.g., airflow related health) reports associated with each person who is a user of the information processing system 200. Such reports can be presented to a user via the user output interface 213, or can be sent to another system or device such as for presentation to another person who is a user of the another system or device. For example, a report indicating a likelihood of imminent severe airflow related health hazard of the person whose airflow related health is being analyzed (e.g., the user of the information processing system 200), can be immediately displayed to the user (e.g., via the user output interface 213) and/or wirelessly sent to another person via at least one of the wireless transceiver 210 and the short range communications circuitry 215, the sent report being destined for reception by another system or device used by another person. Such another person may be, for example and not for limitation, at least one of a parent, physician, teacher, and a friend, of the person whose airflow related health is being analyzed, and optionally the another person may be a medical person and/or a first responder such as fire rescue personnel. In certain embodiments, the sent report is destined for reception by another system or device which is selected at least in part because they are in the vicinity of the information processing system 200.

One or more message packets constituting the report information, as an example, can be destined for reception by another system or device by adding destination address information (e.g., network destination identification information) to the message packets. These message packets can be wirelessly transmitted via at least one of the wireless transceiver 210 and the short range communications circuitry 215 for reception by the destination another system or device in the vicinity of the information processing system 200. In this way, a nearby person may be able to assist the user of the information processing system 200 who is experiencing an imminent severe airflow related health hazard. However, according to certain embodiments, if a user pulmonary health report indicates a non-urgent condition of airflow related health problems for the user of the information processing system 200, then this type of report could be presented to the user via the user output interface 213 (e.g., via the display) to alert the user of the non-urgent condition.

It should be noted that for the message packets to be wirelessly transmitted via at least one of the wireless transceiver 210 and the short range communications circuitry 215 for reception by the destination another system or device, the address information (e.g., network destination identification information) may be stored in the non-volatile memory 206 (such as in the contextual information database 226) and retrieved by the processor 202 for generating the message packets. Optionally, the address information (e.g., network destination identification information) may be maintained in the user pulmonary health tracking database 104 by the corresponding server 102 (see FIG. 1). This address information (e.g., network destination identification information) could be periodically sent to the information processing system 200, or can be sent in response to receiving a request message from the information processing system 200. In this way, each information processing system 200 in the communication system 100 can be continuously updated (or updated each time a request-response message communication is established with the server 102), with current address information (e.g., current network destination identification information) of other systems and devices that are in the vicinity of each other. This address information is stored in the non-volatile memory 206 and readily available to the processor 202 for notifying with reports and other information the other systems and devices in the communication system 100.

In particular, according to various embodiments, the geographic location of each such system and device in the communication system 100 can be tracked by the server 102 and stored in the corresponding database 104. For example, each such system and device can periodically determine its location information and sends this location information to the server 102, which stores the location information in the corresponding database 104. In another example, the NOC 114 can keep track of the location information for each of the wireless devices operating in the wireless communication network N1 112, and periodically send this location information in update messages to the server 102 to maintain the current location information in the corresponding database 104. The server 102 can determine whether information processing systems and devices are in the vicinity of each other, such as by comparing relative location information associated with other systems and devices being tracked in the corresponding database 104. Thereby, the server 102 can update the address information (e.g., network destination identification information) of systems and devices to the other systems and devices in the vicinity.

An example of a user pulmonary health tracking database 104 is shown in FIG. 3. The user pulmonary health tracking database 104 includes records of one or more persons who are users of at least one information processing system 200, such as the mobile phone 110 and the laptop PC 108, in the communication system 100 shown in FIG. 1. Each user record is identified by a user identification code (user ID) 302. The user's record is illustrated by a row in the table 104 as shown. Each user record includes a user pulmonary health current profile 304, which corresponds to the user pulmonary health current profile 220 in the information processing system 200 shown in FIG. 2. Each user record also includes a user pulmonary health history 306, which corresponds to the user pulmonary health history database 222 in the information processing system 200 as shown in FIG. 2. Similarly, each user record includes at least one speech characteristics model 308, which corresponds to the user's speech characteristics model 224 in the information processing system 200 as shown in FIG. 2. Each user record in the user pulmonary health tracking database 104 also includes network identification information 310 for one or more information processing systems 200 that are used by the user associated with the particular user record. It should be noted that, according to various embodiments, the at least one speech characteristics model 308 may comprise a plurality of speech characteristics models 308 corresponding one-to-one with a plurality of information processing systems 200 that are used by the user associated with the particular user record. Each user record in the user pulmonary health tracking database 104 also includes contextual information 312 which corresponds to the contextual information database 226 in the information processing system 200 as shown in FIG. 2. Each user record in the user pulmonary health tracking database 104 also may include other data 314 as shown. The other data 314 can include, for example, personal health information for the particular user, emergency contact information in case of a medical emergency, and other data that may be relevant to managing the user's pulmonary health, as well as determining and/or responding to airflow disease trigger events.

Figure 4:
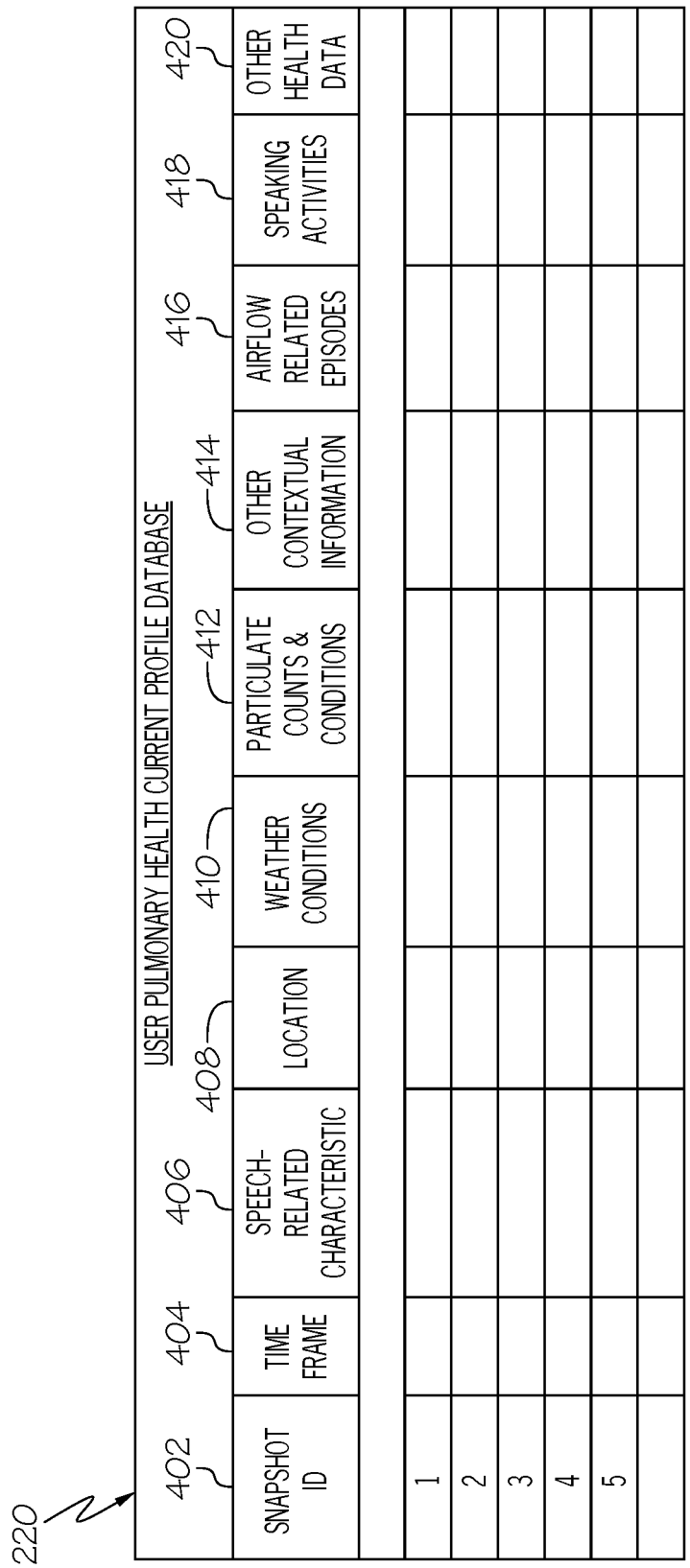
FIG. 4 is a block diagram illustrating an example of a user pulmonary health current profile database as shown in FIG. 2, according to various examples of the present disclosure.

An example of a user pulmonary health current profile database 220 is shown in FIG. 4. The user pulmonary health current profile health database 220 maintains current pulmonary health profile information for each user of the information processing system 200. The pulmonary health profile information may be maintained over a relatively short period of time, such as hours or days. In the example of FIG. 4, five snapshots are shown capturing user pulmonary health current profile data for a user. Each row in the table 220 represents one snapshot. Each row therefore includes a snapshot identification code (snapshot ID) 402 to identify the particular snapshot being stored in the user pulmonary health current profile database 220.

Each snapshot also includes time frame (temporal) information 404 which identifies temporal information associated with the particular snapshot. Each snapshot includes speech-related characteristics 406 that represent the user's speech-related characteristics associated with the particular snapshot. It should be noted that the speech-related characteristics 406 may include a representation of speech-related characteristics information captured from one or more audio samples of the user's verbal communications associated with the particular snapshot. Optionally, the speech-related characteristics 406 may include a pointer to (or a copy of) the user's speech characteristics model 224 that was applicable to an analysis of the user's pulmonary health based at least on the speech-related characteristics information captured from the one or more audio samples of the user's verbal communications and associated with the particular snapshot.

Each snapshot also includes location information 408, weather conditions information 410, particulate counts and conditions 412, and other contextual information 414, associated with the particular snapshot. Additionally, each snapshot includes airflow related episodes information 416 for a user, and speaking activities 418 of the user, that are related to the particular snapshot. Each snapshot may also include other health data 420 of the user that is related to the particular snapshot. A snapshot therefore represents current pulmonary health profile information for a user of the information processing system 200. In certain embodiments, a collection of current snapshots, such as the five snapshots shown in FIG. 4, can be analyzed as a set that represents current pulmonary health profile information for a user. By using a set of multiple snapshots in the user health profile 220 an analysis can compensate for transient noise information affecting one (or a few) of the set of snapshots which thereby results in a more accurate and robust representation of the user's current pulmonary health profile information.

An example of a user pulmonary health history database 222 is shown in FIG. 5. The user pulmonary health history database 222 contains, according to the present example, snapshots information that could be in the near term similar to snapshot information maintained in the user pulmonary health current profile database 220. However, the snapshots information collected over a long period of time, such as for days, weeks, months, or for the life of use of an information processing system by a user, can include a much richer amount of user health history information.

This user health history information can be mined for identifying patterns of information that may be useful for determining trends in data values and for correlations across multiple dimensions (weather, particulate, location, and airflow). Typically this data mining can be performed off-line, such as during periods of low processing activity of the information processing system 200 to help preserve system resources, such as the life of a portable power source (e.g., a battery).

The pulmonary health monitor 218 can use the mined health-related data for dynamically updating the user's speech characteristics model 224 and optionally updating the user pulmonary health current profile database 220. While the data mining operations can be performed off-line over an extended period of time (e.g., during low processing activity of the information processing system 200), the pulmonary health monitor 218 typically uses the user's speech characteristics model 224 to analyze one or more captured audio samples of user data for detecting changes in speech characteristics at, or near, real-time analysis speeds. For example, the analysis of the one or more captured audio samples can be at, or near real-time analysis speeds from the point in time of obtaining the at least one audio sample. This provides a user, and/or other persons such as medical personnel and other first responders, very timely information to more quickly manage (and even proactively manage before an airflow related health episode occurs) any serious airflow health situation of the user being monitored by the pulmonary health monitor 218.

The user pulmonary health history database 222 includes, for each user, a number of snapshots captured and tracked over an extended period of time. Each snapshot stored in the database 222 includes a snapshot identification code (snapshot ID) 502, and a timeframe (temporal information) 504 associated with the particular snapshot.

Each snapshot includes speech-related characteristics 506 associated with the particular snapshot. It should be noted that the speech-related characteristics 506 may include a representation of speech-related characteristics information captured from one or more audio samples of the user's verbal communications associated with the particular snapshot. For example, contours of amplitude change can be extracted from the one or more audio samples collected over a period of time. The contours of amplitude change can be corresponded to changes in an airflow profile of the person. Optionally, the speech-related characteristics 506 may include a pointer to (or a copy of) the user's speech characteristics model 224 that was applicable to an analysis of the user's pulmonary health based at least on the speech-related characteristics information captured from one or more audio samples of the user's verbal communications and associated with the particular snapshot.

Each snapshot includes location 508, weather conditions information 510, particulate counts and conditions 512, and other contextual information 514, associated with the particular snapshot. Additionally, each snapshot includes airflow related episodes information 516 for a user, and speaking activities 518 of the user, that are related to the particular snapshot. Each snapshot may also include other health data 520 of the user that is related to the particular snapshot. A snapshot represents pulmonary health information for a user of the information processing system 200 at the time of the snapshot. The number of snapshots that can be stored in the user pulmonary health history database 222 is limited only by the storage capacity of the non-volatile memory 206.

Figure 6:
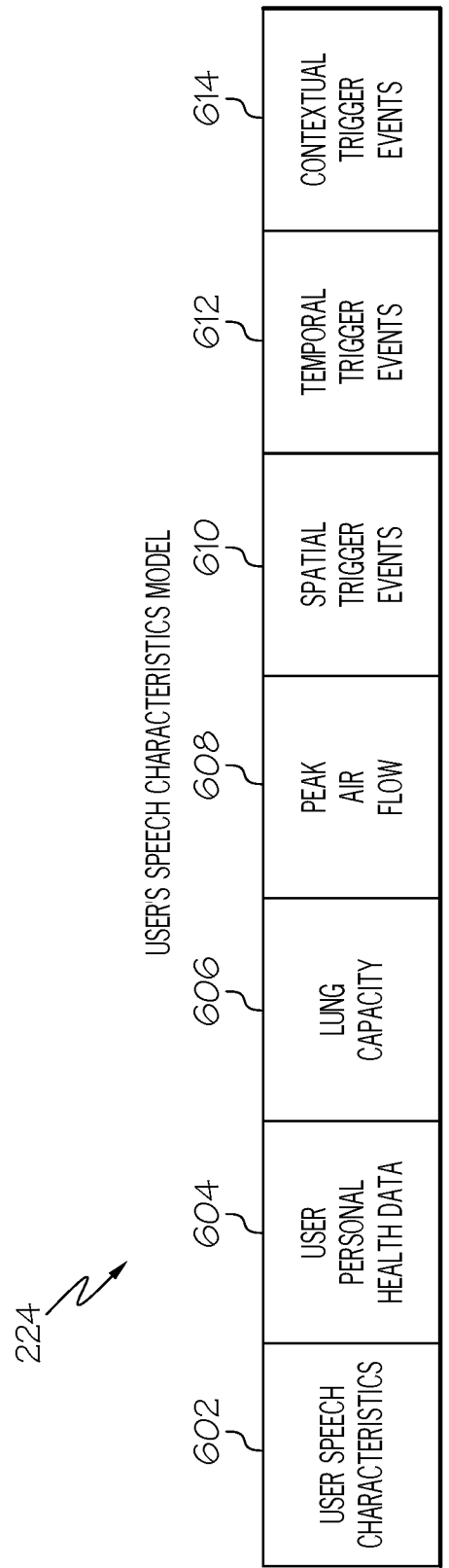
FIG. 6 is a block diagram illustrating an example of a user's speech characteristics model as shown in FIG. 2, according to various examples of the present disclosure.

An example of a user's speech characteristics model 224 is shown in FIG. 6. Such user's speech characteristics model 224 would be maintained for each user of the information processing system 200. The speech characteristics model 224, according to the present example, includes user speech characteristics 602, user personal health data 604, the user's lung capacity 606, the user's peak air flow information 608, spatial trigger events information 610 associated with the user's pulmonary health and airflow disease triggers, temporal trigger events information 612 associated with the user's pulmonary health and airflow disease triggers, and contextual trigger events information 614 associated with the user's pulmonary health and airflow disease triggers.

Figure 7:
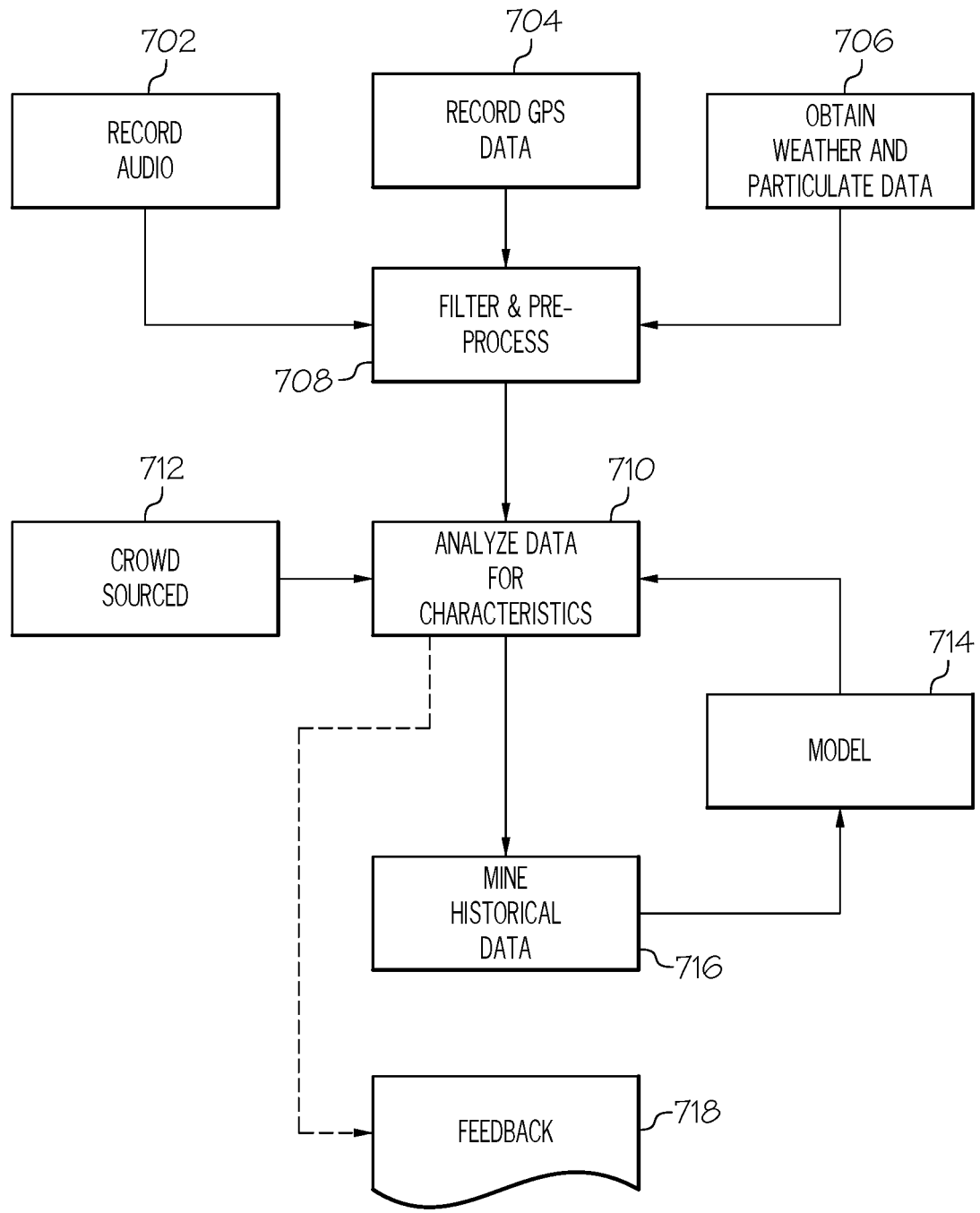
FIG. 7 is a functional block diagram illustrating an example of operations and data flowing used in an information processing system such as shown in FIG. 2, according to various examples of the present disclosure.

Referring to FIG. 7, various functions for an information processing system 200 are illustrated according to one example. The information processing system 200, according to the example, operates with new and novel methods to measure and analyze temporal, spatial, and contextual effects on lung function of a user of the information processing system 200. It should be understood that the information processing system 200 may represent any system or device suitable for operating the novel methods according to the present disclosure, such as at least one of, and not for limitation, the mobile phone 110, the laptop PC 108, an information processing system, a smart phone, a tablet computer, and other systems and devices. In the present example will be used a mobile phone 110 merely for discussion purposes and not for limitation. Changes in a user's speech-related characteristics (e.g., speech-related characteristics representing contours of amplitude change of the user's speech-related audio), based on analyzing audio samples of the user's verbal communications, can be mapped temporally and spatially, and with reference to contextual information, to detect triggers of airflow disease for the user.

According to the present example, various features and functions in a novel process operating with the information processing system 200 (e.g., the mobile phone 110) are outlined below.

1. Record data. (audio, location information, weather and other contextual information, such as particulate matter).
2. Filter and pre-process data.
3. Analyze the data for applicable speech-related characteristics with reference to the user's speech characteristics model.
4. Where applicable, exchange anonymous data with peers and use it for building and updating the user's speech characteristics model.
5. Mine historical data.
6. Update the user's speech characteristics model based on dynamic contextual and/or crowd sourced data.
7. Produce one or more reports for a user as a feedback, and optionally for other person(s).

A more detailed description of the example process outlined above will now be discussed. The processor 202, interoperating with the pulmonary health monitor 218, at step 702, records data (e.g., a user's speech-related audio, location information, and weather and other contextual information, such as particulate matter) by collecting and storing the data in the non-volatile memory 206. The processor 202 collects one or more audio samples from an ambient environment in the vicinity of a microphone in the user output interface 213. Sound audio received by the microphone is recorded whilst the processor 202 determines that a user of the mobile phone 110 is in conversation with others. This can be done at irregular intervals. Geospatial (e.g., geographic) location information of the mobile phone 110, at step 704, and weather conditions and other contextual information related to the location information, such as particulate matter and pollen count information, at step 706, are continuously collected and logged by storing this information in the user pulmonary health current profile database 220, the history database 222, and the contextual information database 226. These locally stored information sources (e.g., the profile database 220, the history database 222, and the contextual information database 226) can be queried by the processor 202 to obtain information that can be used in analyzing speech-related characteristics of collected audio data from the user of the information processing system 200.

Contextual information such as particulate data and pollen count, etc., can be downloaded from information source(s) such as the weather and particulate data server 128 remotely located across the wide area network N2 106. The mobile phone 110 can send request messages (e.g., send a query message) to the remote server 128 and receive response messages therefrom to collect the contextual information. The request messages would typically include at least one of: a representation of the location information of the person and temporal information representing substantially a time of obtaining at least one audio sample of the person's verbal communication. The mobile phone 110 can receive the response messages that include the additional information requested by the mobile phone 110.

In certain embodiments, the pulmonary health monitor server 102 continuously queries the weather and particulate data server 128 (and possibly also queries many other servers that provide other contextual information) by sending request messages to the remote server 128 and receiving response messages therefrom to collect the contextual information and storing the information in the user pulmonary health tracking database 104. The mobile phone 110, periodically can send a request message (e.g., send a query message) to the pulmonary health monitor server 102 and receive a response message with a collection of all the relevant contextual information which the mobile phone 110 can then store/update in the non-volatile memory 206. The mobile phone 110, according to these embodiments, advantageously is relieved from having to continuously send many queries (many request messages) and receive many response messages to-from potentially many different sources of information, e.g., many remote servers, to collect the contextual information. These many exchanges of request messages and response messages by the mobile phone 110, and by many other such information processing systems 200, collectively over a wireless communication network N1 112 can result in inefficient and reduced communication throughput and delayed communication for users of the wireless communication network N1 112. Additionally, the many exchanges of messages by the mobile phone 110 over the wireless communication network N1 112 can be costly and frustrating to the user of the mobile phone 110 by incurring additional data charges and operational delays in collecting the contextual information used by the mobile phone 110.

The processor 202 interoperating with the pulmonary health monitor 218, at step 708, filters and pre-processes the collected and stored data.

The sound audio that is recorded whilst the processor 202 determines that a user of the mobile phone 110 is in conversation with others, is filtered and pre-processed to isolate and extract the user's recorded sound audio from other recorded audio (e.g., background audio, noise audio, and spoken audio from others in the communication).

It should be noted that, according to various embodiments, the pulmonary health monitor 218 in an information processing system 200, e.g., in the mobile phone 110, maintains an inactivity timer with which it tracks a regular time interval during which the user has not been monitored in conversation with others. It is desirable to continuously gather and record audio samples of the user's speech audio to accurately profile the user's speech changes over time. For example, if the user has not been making enough phone calls with the mobile phone 110 for up to a defined inactivity time interval, the pulmonary health monitor 218, via the user interface 212 of the mobile phone 110, can automatically prompt the user to speak any one or more of a defined phrase, one of a plurality of defined phrases, and a randomly selected phrase from a plurality of candidate defined phrases. This would be, for example, some standard phrase that could be spoken by the user to provide voice sample data for the analysis engine in the pulmonary health monitor 218. So, for example, if no incidental recordings of the user's voice during conversation are monitored during some defined time period, the information processing system 200 (e.g., mobile phone 110) could perhaps "call" the user (so the phone actually rings, and the user answers the phone), and the user repeats back some defined phrase upon hearing an audible prompt from the mobile phone 110.

Alternatively, as another example, the mobile phone 110 could notify the user via the user output interface 213, such as by visual indication on a display, to indicate a recording of the user's voice sample is required and, accordingly, displaying a target phrase that the user is requested to speak into the microphone of the mobile phone 110. According to the example, the user's voice audio would be recorded, processed, and analyzed at the time of obtaining the at least one audio sample from the user's voice audio, and accordingly any significant changes in the user's speech characteristics would be updated in the user's speech characteristics model 224 and in the user's health current profile database 220. By continuously gathering and recording audio samples of the user's speech audio the pulmonary health monitor 218 can more accurately profile the user's speech changes over time.

Audio processing techniques to isolate the user's sound audio from other recorded audio are well known to those of ordinary skill in the art. According to various embodiments, for example, the recorded audio that has been pre-processed by audio signal conditioning circuits (e.g., by filtering circuits and equalizing circuits) and digitized (e.g., by using an analog-to-digital converter circuit) is stored in the non-volatile memory 206. The processor 202 can use digital signal processing techniques to further filter and process the digitized audio signal to isolate the user's sound audio from other recorded audio. The user's speech-related characteristics of the recorded user's sound audio can be processed and stored in non-volatile memory 206. The user's sound audio may contain non-voiced audio signal that can be filtered for white noise and categorized for contextual analysis.

For example, the most common symptoms of asthma include shortness of breath, wheezing, chest tightness, and a dry, irritating, continual cough, all caused at least in part by narrowing of the airway that limits airflow. Chronic obstructive pulmonary disease, involves a gradual progression from inflation to the small airways that limits airflow to the destruction of alveolar walls and capillaries which leads to loss of elasticity. Symptoms of emphysema airflow disease include a distinctive cough and shortness of breath. A user's sound audio may include a combination of voiced and non-voiced audio signals that can be filtered for white noise and categorized (e.g., distinctive cough, wheezing, shortness of breath, etc.) for contextual analysis. Particularly the non-voiced audio signals can be categorized such as a distinctive cough, wheezing, and shortness of breath, which can be indicative of the presence of physical airflow disease symptoms.

The processor 202 interoperating with the pulmonary health monitor 218, at step 708, filters and pre-processes the collected and stored weather and other contextual information such as particulate matter and pollen count, to extract relevant contextual information based on geographic location information and temporal information associated with the person who is the user of the mobile phone 110. While the mobile phone 110 is with the person who is the user, the mobile phone 110 can be held stationary or can move with the person following a path along one or more geospatial (e.g., geographic) regions. The effects of an airflow disease trigger on the person can occur at any recent point along the path followed by the person carrying the mobile phone 110. A trigger event can affect the person's speech and airflow health at substantially a time of obtaining the at least one audio sample of the person's verbal communication. However, an earlier trigger event at a time recently before the time of obtaining the at least one audio sample could also affect the person's speech and airflow health at the time of obtaining the audio sample. Therefore, the relevant contextual information can be found based on geographic location information and temporal information for any recent point along the geographic path being followed by the person using the mobile phone 110.

A smart mobile phone 110 is capable of connecting to a wide area network, such as the Internet, wherein the mobile phone 110 will be able to retrieve weather and particulate data associated with the geographic region the user is located at that point in time, or located at a recently previous point in time. The user geographic location can be obtained by the mobile phone 110 such as through assistance from the GPS receiver 211 and/or from using the wireless transceiver 210 operating in a wireless communication network N1 112 and utilizing the location determining services and facilities available from the wireless network, such as available using any one or more of cellular networks, Wi-Fi communication, and/or other geographic location services accessible by the mobile phone 110. For example, one or more sensors in the mobile phone 110 can detect when in proximity to location identification devices in the vicinity of the mobile phone 110. In certain embodiments, at least one of the GPS receiver 211 and the wireless transceiver 210, communicatively coupled with the processor 202, can be used to obtain the geographic information of the person. This geographic information can include a determined geographic location (or a plurality of geographic locations) of the person along a path being traveled by the person up to substantially a time of obtaining the at least one audio sample of the person's verbal communication.

According to the present example, the preprocessing stage, at step 708, involves the quantification of the filtered sound channels (voiced and non-voiced), the weather data, and the particulate data. These values are then used by the processing stage for analysis, as will be discussed below.

According to the present example, the processor 202 interoperating with the pulmonary health monitor 218, at step 710, analyzes the data for applicable changes in the user's speech-related characteristics in the sampled audio with reference to the user's speech characteristics model 224. The processor 202, for example, extracts contours of amplitude change from the at least one audio sample over a period of time, the contours of amplitude change corresponding to changes in an airflow profile of the person. The airflow profile information of the person is stored in at least one of the user's speech characteristics model 224 and the user pulmonary health current profile database 220.

Contextual audio data, which can include the level of background noise, and non-voiced data such as coughing and wheezing, could also be detected. Besides contextual audio data, the geographic location data is analyzed to augment the accuracy of analysis using the user's speech characteristics model 224. The geographic locations that the user visited in the past, the user's location whilst talking, the prevalence of particulate matter in those geographic locations, the duration of the person's stay at the visited geographic locations, the weather conditions at the times of the visit, and the amount of activity (number of phone calls, meetings, etc.) the person made during those times, and so forth, are sources of contextual data taken into account while deriving the changes in the user's speech-related characteristics as compared to the user's speech characteristics model 224.

Speech-related characteristics from the at least one audio sample will be recorded including values produced by analyzing such speech-related characteristics as volume, tempo, intonation, emphasis, sentence and word length, and other speech-related characteristics. Fluctuations in sound amplitude, when they happen during a speech, are often associated with the effect of any, or a combination, of: dyspynea, sibilant rhonchi, aphasia, or any health issues that affects he person's airflow. In order to quantify this association, the processor 202 interoperates with the pulmonary health monitor 218 to extract contours of audio amplitude change over a period of time that could be directly mapped to changes in the airflow profile of a person—after dynamic normalization of sound volume during the analysis of the one or more audio samples. The processor 202 correlates sound amplitude fluctuation with periodic/non-periodic episodes related to aforementioned airflow related health problems. The processor, at step 710, also correlates the sound amplitude fluctuations with contextual data, such as: weather data, particulate data, and user geographic location information.

The processor 202, at step 712, where applicable exchanges anonymous crowd sourced data with information processing systems and devices of other persons (e.g., peers of the user of the mobile phone 110). This anonymous data can be collected off-line by the mobile phone 110, and used to update the user pulmonary health current profile 220, the history database 222, and the user's speech characteristics model 224. Sensing the background contextual data is also managed by exchanging anonymous data with peers when those peers are in vicinity with the user of the mobile phone 110. For instance, other users (via their information processing systems and devices such as their mobile phones 110, laptop PCs 108, etc.) could send contextual information on geographic locations where they have detected airflow disease triggers for themselves as well as how their condition is trending and/or any experiences of acute airflow disease events. The crowd sourced information received by the mobile phone 110 can indicate where a trigger has been detected that detrimentally has affected airflow related health of another person at the location of the other person and/or at a location along a path followed by the mobile phone 110 being carried by the user of the mobile phone 110.

The processor 202, at step 716, can mine historical data in the user pulmonary health history database 222, and use this information to update the user's speech characteristics model 224. Historical data can be mined for detecting trends, correlations across multiple dimensions (e.g., weather conditions, presence of airborne particulates, geographic location, and airflow conditions of the user). The mined data is then used for dynamically updating the user's speech characteristics model 224 that is normally used to analyze the user's collected and stored data for determining changes in the user's speech-related characteristics at real-time. Historic data mining, at step 716, can be done using offline processing such as when the processor 202 is in a low activity state, as compared to the analysis of user data, at step 710, for determining changes in speech-related characteristics at, or near, real-time.

The processor 202, at step 714, can use the mined data to update user speech characteristics model 224. A model of the user's speech characteristics 224 is built and updated based on the characteristics of the user's speech, how these characteristics relate to pulmonary health and capacity, and how these characteristics relate to the other contextual information stored in the non-volatile storage 206, as has been discussed above. This user's speech characteristics model 224 is created from user data as well as known constants, and can be used to determine relative differences in the pulmonary health of the user. The model's output may include estimates for lung capacity and peak airflow of the user, spatial information (e.g., geographic location information) associated with the user carrying the mobile phone 110 on their person, temporal information associated with the user using the mobile phone 110, and contextual trigger events that are related to the user.

The processor 202, at step 718, can provide feedback by reports that are stored in the user reports repository 216 and provided (e.g., displayed) to the person using the mobile phone 110, and optionally to other persons. The results of the continuous analysis, at step 710, is stored locally in the non-volatile memory 206 and/or sent to the remote pulmonary health monitor server 102 for storage at the corresponding user pulmonary health tracking database 104.

The user of the mobile phone 110 can be continuously provided, at step 718, with the user's performance reports related to their airflow health. These reports can include temporal, spatial, geographical, as well as contextual information that can provide comprehensive information for anyone to identify any potential triggers for airflow related diseases and/or existing problems. The reported values in the feedback are all based on dynamic computation of the user model 224 as correlated to changes in the user's speech-related characteristics associated with the one or more audio samples collected from the user's speech-related audio, and that takes into account the user's contextual and historical data that are stored in the non-volatile storage 206.

The feedback report, while not detecting an urgent health hazard condition, is provided at regular intervals when there is less likelihood of any immediate effect to the user. When the prognosis is more urgent, indicating a likelihood of severe airflow health hazard to the user, such as an asthma attack, the feedback report can be instantaneous. In the latter case, the urgent report could also be shared with the peers (e.g., other information processing systems 200 being used by other persons) around the physical geographic vicinity of the user, that have been tracked through crowd sourcing of information, at step 712.

In summary, the processor 202 produces an airflow health report, based at least on the correlating the contours of amplitude change with periodic episodes typical of airflow related health problems and on the determining whether the contours of amplitude change result from at least one local environmental factor (e.g., an airflow disease trigger) related to the geographic information (e.g., the geographic location of the mobile phone 110 at the time of collecting the audio sample from the user or in the recent past previous to collecting the audio sample).

The report is produced and presented at a regular interval, based on the correlating and determining indicating a non-urgent condition of airflow related health problems. Alternatively, the report is produced and presented to the user, based on the correlating and determining, the report being presented contemporaneously with the correlating and determining indicating a likelihood of imminent severe airflow related health hazard for the user. Additionally, the report can be presented to another person (e.g., to peers, professional medical personnel, doctors, nurses, emergency rescue personnel, etc.) in the vicinity of the person whose airflow related health is being analyzed, contemporaneously with the correlating and determining indicating a likelihood of imminent severe airflow related health hazard affecting the person.

The presenting, according to various embodiments, can include one or more of: displaying the report on at least one of: a display of a mobile phone, a display of an information processing system; a display of a laptop personal computer; and a display of a tablet computer.

NON-LIMITING EXAMPLES

As will be appreciated by one skilled in the art, aspects of the present disclosure may be embodied as a system, method, or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit", "module", or "system."

Various embodiments of the present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present disclosure are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the computer readable storage medium is shown in an example embodiment to be a single medium, the term "computer readable storage medium" should be taken to include a single medium or multiple media (e.g., a centralized or distributed database, and/or associated caches and servers) that store the one or more sets of instructions. The term "computer-readable storage medium" shall also be taken to include any non-transitory medium that is capable of storing or encoding a set of instructions for execution by the machine and that cause the machine to perform any one or more of the methods of the subject disclosure.

The term "computer-readable storage medium" shall accordingly be taken to include, but not be limited to: solid-state memories such as a memory card or other package that houses one or more read-only (non-volatile) memories, random access memories, or other re-writable (volatile) memories, a magneto-optical or optical medium such as a disk or tape, or other tangible media which can be used to store information. Accordingly, the disclosure is considered to include any one or more of a computer-readable storage medium, as listed herein and including art-recognized equivalents and successor media, in which the software implementations herein are stored.

Although the present specification may describe components and functions implemented in the embodiments with reference to particular standards and protocols, the disclosure is not limited to such standards and protocols. Each of the standards represents examples of the state of the art. Such standards are from time-to-time superseded by faster or more efficient equivalents having essentially the same functions.

The illustrations of examples described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Although specific embodiments have been illustrated and described herein, it should be appreciated that any arrangement calculated to achieve the same purpose may be substituted for the specific embodiments shown. The examples herein are intended to cover any and all adaptations or variations of various embodiments. Combinations of the above embodiments, and other embodiments not specifically described herein, are contemplated herein.

The Abstract is provided with the understanding that it is not intended be used to interpret or limit the scope or meaning of the claims. In addition, in the foregoing Detailed Description, various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

Although only one processor 202 is illustrated for information processing system 200, information processing systems with multiple CPUs or processors can be used equally effectively. Various embodiments of the present disclosure can further incorporate interfaces that each includes separate, fully programmed microprocessors that are used to off-load processing from the processor 202. An operating system (not shown) included in main memory for the information processing system 200 may be a suitable multitasking and/or multiprocessing operating system, such as, but not limited to, any of the Linux, UNIX, Windows, and Windows Server based operating systems. Various embodiments of the present disclosure are able to use any other suitable operating system. Some embodiments of the present disclosure utilize architectures, such as an object oriented framework mechanism, that allows instructions of the components of operating system (not shown) to be executed on any processor located within the information processing system. Various embodiments of the present disclosure are able to be adapted to work with any data communications connections including present day analog and/or digital techniques or via a future networking mechanism.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. The term "another", as used herein, is defined as at least a second or more. The terms "including" and "having," as used herein, are defined as comprising (i.e., open language). The term "coupled," as used herein, is defined as "connected," although not necessarily directly, and not necessarily mechanically. "Communicatively coupled" refers to coupling of components such that these components are able to communicate with one another through, for example, wired, wireless or other communications media. The term "communicatively coupled" or "communicatively coupling" includes, but is not limited to, communicating electronic control signals by which one element may direct or control another. The term "configured to" describes hardware, software or a combination of hardware and software that is adapted to, set up, arranged, built, composed, constructed, designed or that has any combination of these characteristics to carry out a given function. The term "adapted to" describes hardware, software or a combination of hardware and software that is capable of, able to accommodate, to make, or that is suitable to carry out a given function.

The terms "controller", "computer", "processor", "server", "client", "computer system", "computing system", "personal computing system", "processing system", or "information processing system", describe examples of a suitably configured processing system adapted to implement one or more embodiments herein. Any suitably configured processing system is similarly able to be used by embodiments herein, for example and not for limitation, a personal computer, a laptop personal computer (laptop PC), a tablet computer, a smart phone, a mobile phone, a wireless communication device, a personal digital assistant, a workstation, and the like. A processing system may include one or more processing systems or processors. A processing system can be realized in a centralized fashion in one processing system or in a distributed fashion where different elements are spread across several interconnected processing systems.

The term "geographic information" means any one or more of "geographic location information", "temporal information", and a combination of both space and time information such as "a geospatial location at substantially a point in time", "a geographic location at substantially a point in time", "one or more geospatial locations within a time interval", and "one or more geographic locations within a time interval", and the like. As an example, and not for limitation, use of the term geographic information may include "at this time of the year a geographic location of the person whose airflow health is being monitored".

The corresponding structures, materials, acts, and equivalents of all means or step plus function elements in the claims below are intended to include any structure, material, or act for performing the function in combination with other claimed elements as specifically claimed. The description herein has been presented for purposes of illustration and description, but is not intended to be exhaustive or limited to the examples in the form disclosed. Many modifications and variations will be apparent to those of ordinary skill in the art without departing from the scope of the examples presented or claimed. The disclosed embodiments were chosen and described in order to explain the principles of the embodiments and the practical application, and to enable others of ordinary skill in the art to understand the various embodiments with various modifications as are suited to the particular use contemplated. It is intended that the appended claims below cover any and all such applications, modifications, and variations within the scope of the embodiments.

What is claimed is:

1. An information processing system capable of analyzing airflow related health of a person, the information processing system comprising:
    a microphone circuit of the information processing system for capturing audio signals from an ambient environment in a vicinity of the information processing system and converting the audio signals to electronic audio signals;
    audio conditioning and processing circuitry, coupled with the microphone circuit and a processor of the information processing system, comprising analog-to-digital conversion circuits for converting the electronic audio signals to digitized audio signals, the digitized audio signals representative of the captured audio signals comprising at least one audio sample of a person's verbal communication while the person is using the information processing system at a geographic location;
    memory for storing the digitized audio signals;
    non-volatile memory for storing data and computer instructions;
    a GPS receiver for obtaining geographic information associated with the geographic location of the information processing system;
    a pulmonary health monitor, communicatively coupled with the non-volatile memory;
    a pulmonary health current profile stored in the non-volatile memory;
    a pulmonary health history database stored in the non-volatile memory;
    a speech characteristics model stored in the non-volatile memory; and
    the processor being communicatively coupled with the memory, the non-volatile memory, the GPS receiver, and the pulmonary health monitor, and wherein the processor, responsive to executing computer instructions, performs operations comprising:
        capturing, with the microphone circuit and the audio conditioning and processing circuitry, digitized audio signals representative of the captured at least one audio sample of the person's verbal communication while the person is using the information processing system at a geographic location;
        storing in the memory the captured digitized audio signals;
        obtaining, with the GPS receiver, geographic information indicative of the geographic location of the information processing system while capturing the digitized audio signals representative of the captured at least one audio sample of the person's verbal communication, and associating the geographic information with the captured digitized audio signals representative of the captured at least one audio sample of the person's verbal communication;
        querying at least an additional source of information, that is external to the information processing system, and as a result of the querying, receiving additional information, the received additional information being related to the geographic information;
        extracting contours of audio amplitude change from the digitized audio signals representative of the captured at least one audio sample of the person's verbal communication, the contours of amplitude change corresponding to changes in an airflow profile of the person, the airflow profile of the person being stored in at least one of the speech characteristics model or the pulmonary health current profile;
        correlating the contours of audio amplitude change with at least one of data stored in the pulmonary health current profile or data stored in the pulmonary health history database, the stored data including information associated with episodes typical of airflow related health problems of the person;
        determining, based at least on the additional information and the correlating of the contours of audio amplitude change, whether the contours of audio amplitude change result from at least one local environmental factor related to the geographic information, and wherein the receiving additional information comprises receiving crowd sourced information received by the information processing system exchanging anonymous data with peer information processing systems, the received crowd sourced information comprising identification of at least one geographic location where an airflow disease trigger has been detected by an information processing system of another person and that detrimentally has affected airflow related health of the another person at the at least one geographic location; and continuously providing to the person, via a user interface of the information processing system, performance reports related to the person's airflow health while using the information processing system, the performance reports being based on at least one of:

the contours of amplitude change extracted from the digitized audio signals representative of the captured at least one audio sample of the person's verbal communication and correlated with periodic episodes typical of airflow related health problems for the person, or the crowd sourced information.

2. The information processing system of claim 1, wherein the processor, responsive to executing computer instructions, performs operations comprising:

producing a report, based at least on the correlating and on the determining, of the airflow related health of the person; and presenting the report via the user interface.

3. The information processing system of claim 2, wherein the user interface comprises a display, and wherein the presenting comprises displaying the report on the display of the information processing system.

4. The information processing system of claim 2, wherein the determining is at, or near, real-time analysis speeds after the capturing of the at least one audio sample, and wherein the presenting comprises at least one of:

presenting the report at a regular interval, based on the correlating and determining indicating a non-urgent condition of airflow related health problems; and presenting, based on the correlating and determining, the report contemporaneously with the correlating and determining indicating a likelihood of imminent severe airflow related health hazard.

5. The information processing system of claim 1, further comprising at least one of a wireless transceiver and short range communications circuitry, communicatively coupled with the processor, and wherein the processor, responsive to executing computer instructions, performs operations comprising:

producing a report, based at least on the correlating and on the determining, of the airflow related health of the person; and wirelessly sending the report via the at least one of the wireless transceiver and the short range communications circuitry, destined for reception by a second information processing system in the vicinity of the information processing system, based on the correlating and determining indicating a likelihood of imminent severe airflow related health hazard of the person whose airflow related health is being analyzed.

6. The information processing system of claim 5, wherein the determining is at, or near, real-time analysis speeds from the obtaining of the at least one audio sample, and wherein the processor, responsive to executing computer instructions, performs operations comprising:

presenting, based on the correlating and determining, the report via the user interface contemporaneously with the correlating and determining indicating a likelihood of imminent severe airflow related health hazard of the person whose airflow related health is being analyzed.

7. The information processing system of claim 1, further comprising a wireless transceiver, communicatively coupled with the processor, and wherein the obtaining the geographic information comprises determining, using the wireless transceiver, a geographic location of the person along a path being traveled by the person up to substantially a time of obtaining the at least one audio sample of the person's verbal communication.

8. The information processing system of claim 7, wherein the processor, responsive to executing computer instructions, performs operations comprising:

wirelessly sending, using the wireless transceiver, a request message to a remote server, the request message including at least one of:

a representation of the geographic location information of the person; and temporal information associated with substantially a time of capturing the at least one audio sample of the person's verbal communication; and wherein the receiving additional information comprises:

receiving a response message from the remote server, the response message including additional information.

\* \* \* \* \*